US005562617A

United States Patent [19]
Finch, Jr. et al.

[11] Patent Number: 5,562,617
[45] Date of Patent: Oct. 8, 1996

[54] IMPLANTABLE VASCULAR DEVICE

[76] Inventors: Charles D. Finch, Jr., 112 Water Oaks Dr., Clinton, Miss. 39056; Hendrik K. Kuiper, P.O. Box 348, Edwards, Miss. 39066

[21] Appl. No.: 183,151

[22] Filed: Jan. 18, 1994

[51] Int. Cl.$^6$ .................... A61M 11/00; A61M 5/00
[52] U.S. Cl. ................ 604/93; 604/175; 604/183; 604/247; 604/905; 623/1
[58] Field of Search ................ 604/9, 93, 175, 604/183, 244, 247, 891.1, 905; 623/1

[56] References Cited

U.S. PATENT DOCUMENTS

| | | |
|---|---|---|
| 274,447 | 3/1883 | Kenish . |
| 3,331,371 | 7/1967 | Rocchi et al. . |
| 3,888,249 | 6/1975 | Spencer . |
| 4,108,173 | 8/1978 | Slivenko . |
| 4,417,888 | 11/1983 | Cosentino et al. ............ 604/175 |
| 4,484,912 | 11/1984 | Raible ............................. 604/175 |
| 4,496,350 | 1/1985 | Cosentino ...................... 604/175 |
| 4,543,088 | 9/1985 | Bootman et al. ................. 604/93 |
| 4,549,879 | 10/1985 | Groshong et al. .............. 604/247 |
| 4,657,536 | 4/1987 | Dorman ........................... 604/247 |
| 4,671,796 | 6/1987 | Groshong et al. .............. 604/247 |
| 4,673,394 | 6/1987 | Fenton, Jr. et al. ............. 604/175 |
| 4,685,905 | 8/1987 | Jeanneret nee Aab ......... 604/247 |
| 4,692,146 | 9/1987 | Hilger ............................... 604/93 |
| 4,701,166 | 10/1987 | Groshong et al. .............. 604/247 |
| 4,704,103 | 11/1987 | Stöber et al. ................... 604/175 |
| 4,705,501 | 11/1987 | Wigness et al. .................. 604/43 |
| 4,759,752 | 7/1988 | Stöber ............................. 604/247 |
| 4,772,270 | 9/1988 | Wiita et al. ..................... 604/175 |
| 4,802,885 | 2/1989 | Weeks et al. ...................... 604/93 |
| 4,846,806 | 7/1989 | Wigness et al. ................ 604/175 |
| 4,892,518 | 1/1990 | Cupp et al. ........................ 604/93 |
| 4,973,319 | 11/1990 | Melsky ............................ 604/247 |
| 5,030,210 | 7/1991 | Alchas ............................ 604/247 |
| 5,041,098 | 8/1991 | Loiterman et al. ............. 604/175 |
| 5,057,084 | 10/1991 | Ensminger et al. ............ 604/167 |
| 5,112,301 | 5/1992 | Fenton, Jr. et al. ............... 604/30 |
| 5,156,600 | 10/1992 | Young ............................. 604/247 |
| 5,176,627 | 1/1993 | Watson .............................. 604/9 |
| 5,180,365 | 1/1993 | Ensminger et al. .............. 604/93 |
| 5,203,771 | 4/1993 | Melker et al. ................... 604/53 |
| 5,224,938 | 7/1993 | Fenton, Jr. ...................... 604/247 |
| 5,263,930 | 11/1993 | Ensminger ....................... 604/93 |
| 5,290,263 | 3/1994 | Wigness ......................... 604/247 |
| 5,306,255 | 4/1994 | Haindl ............................. 604/175 |
| 5,318,545 | 6/1994 | Tucker ............................ 604/244 |
| 5,336,194 | 8/1994 | Polaschegg et al. ........... 604/175 |
| 5,350,360 | 9/1994 | Ensminger et al. .............. 604/93 |
| 5,360,407 | 11/1994 | Leonard .......................... 604/175 |
| 5,399,168 | 3/1995 | Wadsworth, Jr. et al. ..... 604/175 |

FOREIGN PATENT DOCUMENTS 228532  7/1987  European Pat. Off. .

OTHER PUBLICATIONS

Transactions of American Society for Artificial Internal Organs vol. 28, 14 Apr. 1982—16 Apr. 1982; Chicago Illinois, pp. 54–57; International Search Report.

*Primary Examiner*—Mary Beth Jones
*Attorney, Agent, or Firm*—Phelps Dunbar

[57] ABSTRACT

An implantable device grafted directly to vascular structures for high volume blood and/or fluid infusion and/or removal for such purpose as hemodialysis, apheresis, exchange transfusion, or large volume fluid infusion. The device is also adaptable to intermittent access to the venous or arterial circulations for purpose of blood sampling or giving medications. The device is comprised of an implantable fluid chamber connected to a vascular shunt which is then grafted directly to the vascular structure (e.g. artery or vein). The vascular end of the device employs a valve to prevent reflux of blood and subsequent washout of anticoagulant during periods when the device is not in use. The device is accessed percutaneously with a needle or needle-introduced catheter and is filled with anti-coagulant prior to needle withdrawal to prevent thrombosis.

2 Claims, 4 Drawing Sheets

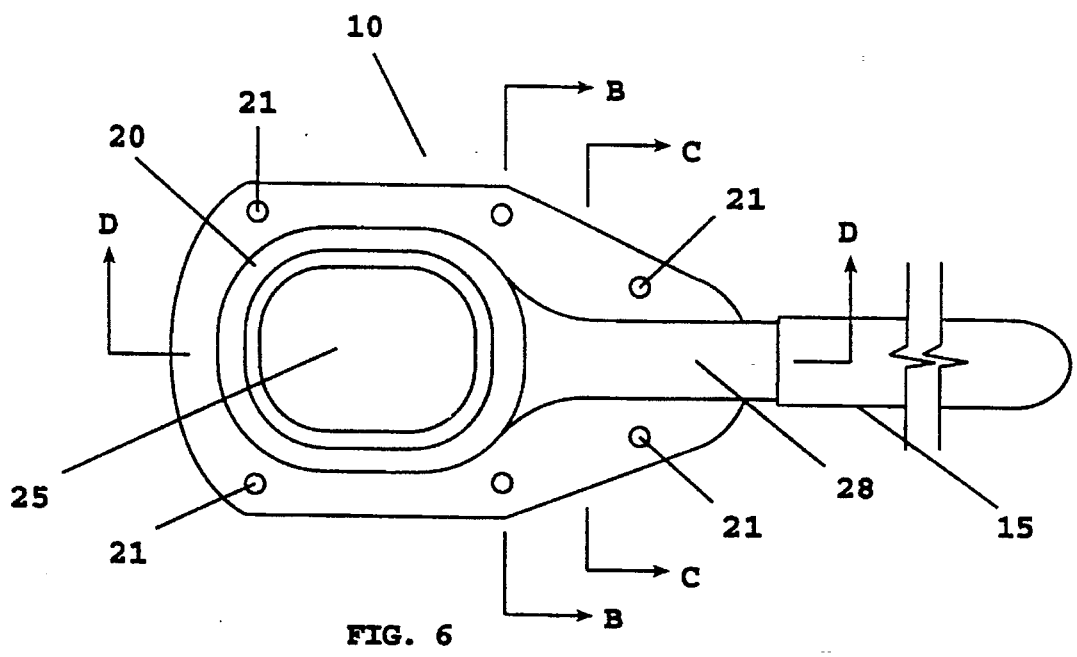
FIG. 6
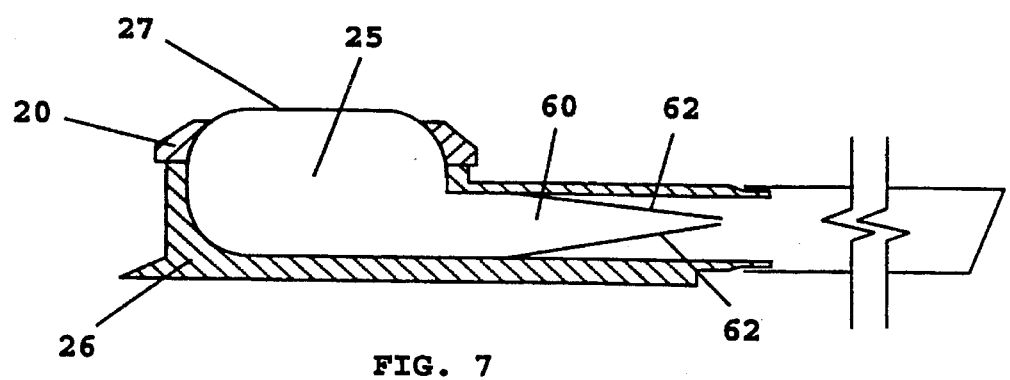
FIG. 7
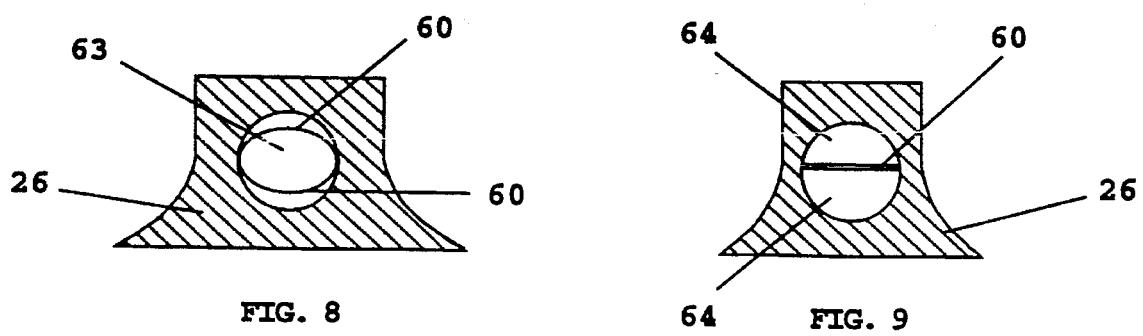
FIG. 8
FIG. 9

IMPLANTABLE VASCULAR DEVICE

BACKGROUND OF THE INVENTION

1. The Field of Invention

The present invention relates to implantable vascular devices for the purpose of access to the body's circulation. More particularly, this invention provides a novel means for intermittent vascular access without the use of indwelling catheters or constant flow shunt structures thus reducing the thrombotic and hemodynamic consequences of other available devices.

2. Related Art

The advent of hemodialysis for the treatment of End-stage Renal Disease has prompted the development of many vascular access devices for the purpose of acquiring large quantities of blood for passage through an extra-corporeal circuit during the hemodialysis procedure. Available devices have consisted of devices employing indwelling venous catheters or flow through shunt devices which create an artificial fistula between an artery and vein.

Current catheter technologies are limited by relatively poor flows and by their tendency to be irritative resulting in vessel stenosis, thrombosis, and occasionally vessel perforation. They frequently dysfunction for mechanical reasons related to the vessel wall, catheter positioning, or thrombus formation in the catheter lumen. For catheter devices that are partially external, infections are frequent due to the chronic breach in the skin, often with severe or even fatal consequences.

Flow through shunt devices which cream a fistulous connection between artery and vein have been the mainstay of modem vascular access for dialysis. These devices are likewise fraught with hazards. Installation of these "shunts" is an extensive surgical procedure resulting in significant tissue trauma and pain. Once in place, the shunts result in additional cardiac output needs with as much as one-fifth of the cardiac output (approximately 1000 ml per minute) required for adequate function. In addition, the transfer of the arterial pressure wave results in damage to the vein at the anastomosis with the shunt resulting in intimal hyperplasia and subsequent shunt occlusion or thrombosis. When this occurs, another vein segment must be used for shunt revision, and exhaustion of available sites is distressingly common. The expense both in terms of health care dollars and human misery is enormous. Repeated punctures of the wall of the shunt result in eventual failure and surgery to repair or replace the shunt.

Each of the available access technologies mentioned thus far are also complicated by the possibility of recirculation of blood already passed through the extra-corporeal circuit resulting in loss of treatment efficiency. The harm done to patients by the "recirculation syndrome" is insidious and at times undetected until great harm has been done.

SUMMARY OF THE INVENTION

The invention enables one to access both the arterial and venous circulations separately, without fistulous communication, thus eliminating recirculation completely and reducing dramatically the demands on the heart. The increased flow to the venous structures would likewise be greatly reduced as would the damaging pressures transmitted to the vascular wall. The invention does not require indwelling catheters and thus eliminates the complications associated with these devices.

Installation of the invention requires surgical implantation but with far less tissue disruption than shunt devices and has the further advantage of allowing arterial and venous ports at anatomically remote sites. Since the invention is totally subcutaneous, infectious complications encountered by partially external catheter devices are avoided. Also, thrombosis of the distal ends of the invention is prevented eliminating a potential nidus of infection and avoiding occlusion while allowing for blood flows adequate for treatment of blood in extra-corporeal circuits for hemodialysis, apheresis, phototherapy, etc.

Most research to date has focused on applications of catheter technology or implantable devices involving constant arteriovenous flow. The invention is the first to employ direct vascular anastomosis using separate implantable ports while allowing for intermittent flow occurring only during extra-corporeal blood treatment. This also provides a means for intermittent access to both arterial and venous circulations without intrusion into the vessel lumen for such purposes as blood sampling or intermittent infusion.

These ends are accomplished by attaching an implantable access port to an acceptable blood vessel by way of a non-collapsible cannula or shunt segment which is then grafted to the vessel wall usually in an "end to side" manner. At the point of anastomosis the invention employs a valve device to prevent reflux of blood and the dilution of anticoagulant when the device is not in use. In its unused state the static nature of the fluid in the device prevents the entry of blood across the valve until the valve is opened and negative or positive pressure is generated by cannulation of the access port.

One embodiment of the invention employs a replaceable dome of penetrable material through which an appropriately designed needle can be placed through the skin and the dome into an underlying chamber which is joined in sequence to a non-collapsible cannula or shunt segment made of PTFE or other suitable material. The vascular end of that segment is joined in sequence to a slit valve device made of Teflon or another suitable material which is, in turn, joined in sequence to the vessel wall, employing a shallow cuff made of PTFE or another suitable material. An alternative construction of this embodiment also employs a flap valve device either in addition to or in place of the slit valve device.

Another embodiment of the invention employs a dual chamber device. One chamber is used for access to the circulation while the other serves as a means to inject sterile fluid for the inflation of a balloon valve residing at the junction of the invention with the vessel wall.

BRIEF DESCRIPTION OF THE DRAWINGS

FIG. 6 shows a top view of an alternative construction of the embodiment of FIG. 1.

FIG. 7 shows a cross section of an alternative construction of the embodiment of FIG. 1 along line D—D.

FIG. 8 shows a cross section of an alternative construction of the embodiment of FIG. 1 along line B—B.

FIG. 9 shows a cross section of an alternative construction of the embodiment of FIG. 1 along line C—C.

FIG, 15 illustrates two implantable vascular devices of the present invention, one connected to a vein, and one connected to an artery, as part of a method for extra-corporeal blood treatment.

DETAILED DESCRIPTION OF THE PREFERRED EMBODIMENTS

Figure 1:
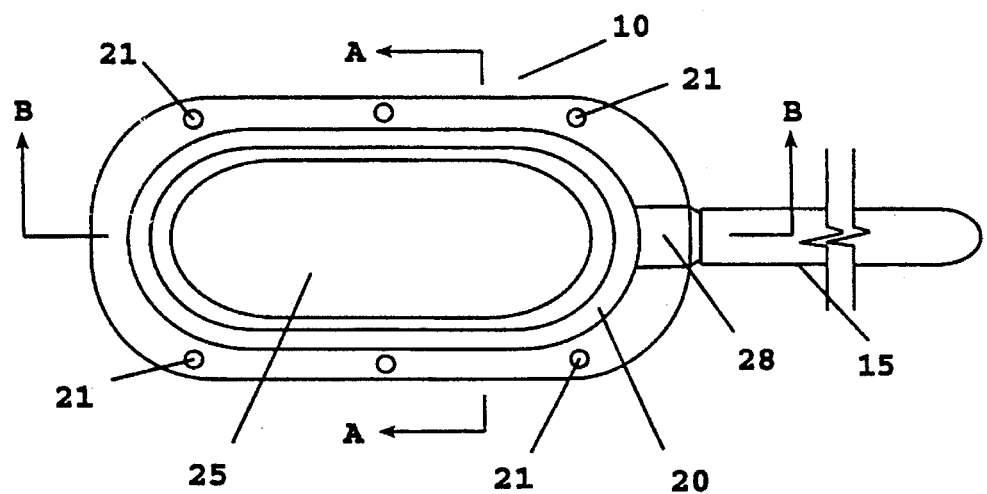
FIG. 1 shows a top view of the first embodiment of the present invention.
Figure 2:
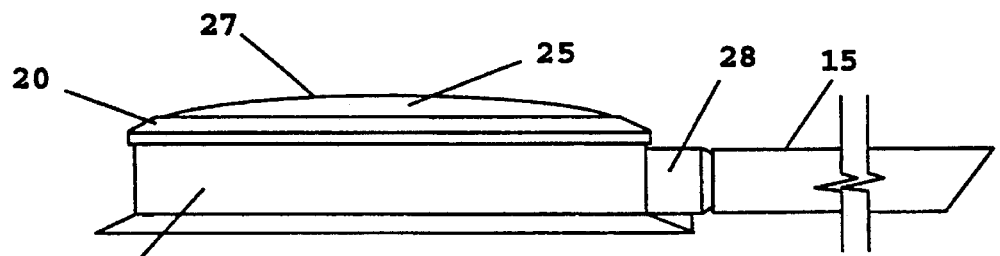
FIG. 2 shows a side view of the embodiment of FIG. 1.
Figure 4:
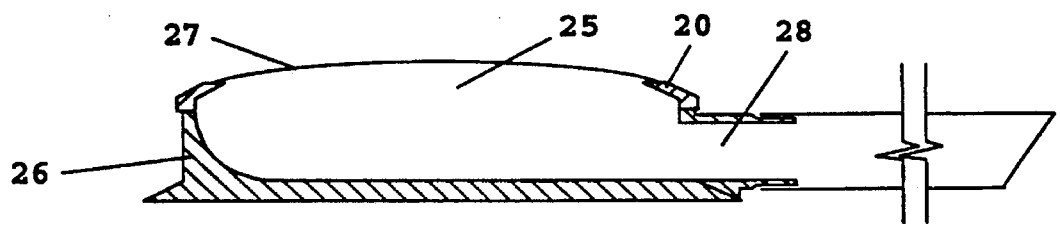
FIG. 4 shows a cross section of the embodiment of FIG. 1 along line B—B.
Figure 3:
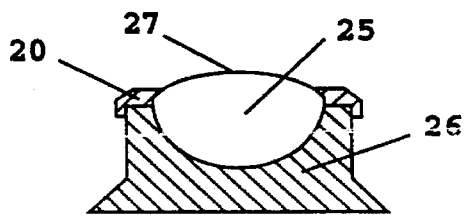
FIG. 3 shows a cross section of the embodiment of FIG. 1 along line A—A.

Referring to FIG. 1 there is depicted a first preferred embodiment of the present invention. This embodiment is an implantable vascular device 10 employing a single hematologic chamber 25. The base and sides of the hematologic chamber 25 are formed by the walls of the body 26 of the device 10. As is best seen in FIGS. 2, 3, and 4, the body 26 is shaped so as to define the base and sides of the hematologic chamber 25, and is further shaped to accept a cover 20. The cover 20 serves to hold in position a replaceable diaphragm 27, which forms the top of the hematologic chamber 25. The cover 20 and body 26 are shaped to allow for easy removal of the cover 20 if replacement of the diaphragm 27 is needed. The base of the body 26 is provided with a flange containing a plurality of apertures 21. These apertures 21 are intended to facilitate fastening of the device 10 to the underlying tissues (not shown). Such fastening will typically be by use of sutures, but may be by any suitable method.

Figure 5:
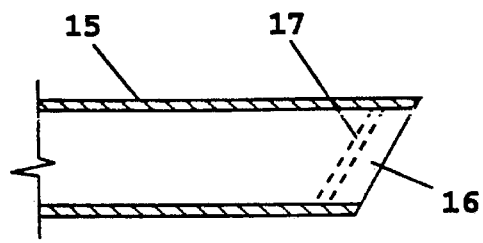
FIG. 5 shows detail of an end of the embodiment of FIG. 1.
Figure 10:
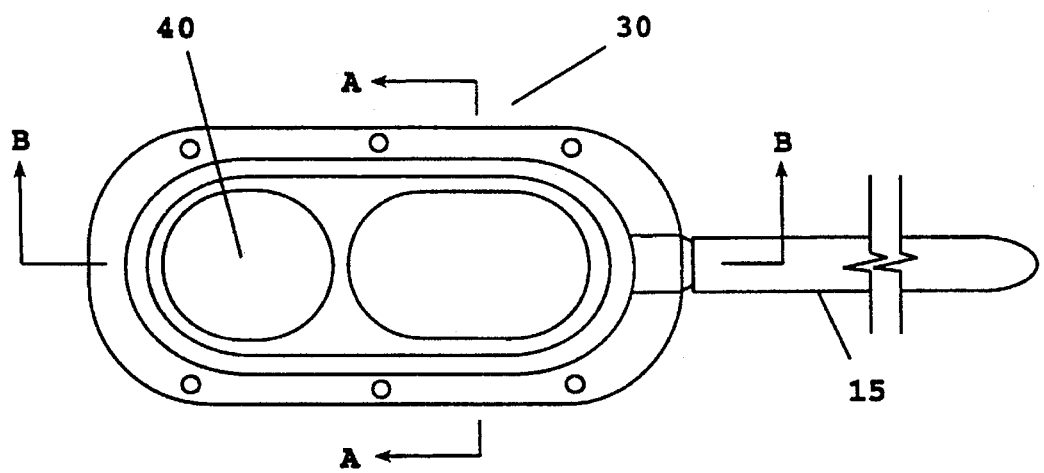
FIG. 10 shows a top view of another embodiment of the present invention.
Figure 11:
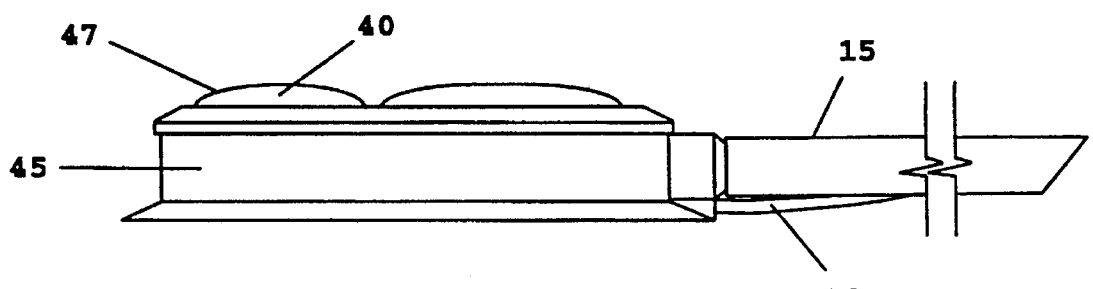
FIG. 11 shows a side view of the embodiment of FIG. 10.
Figure 12:
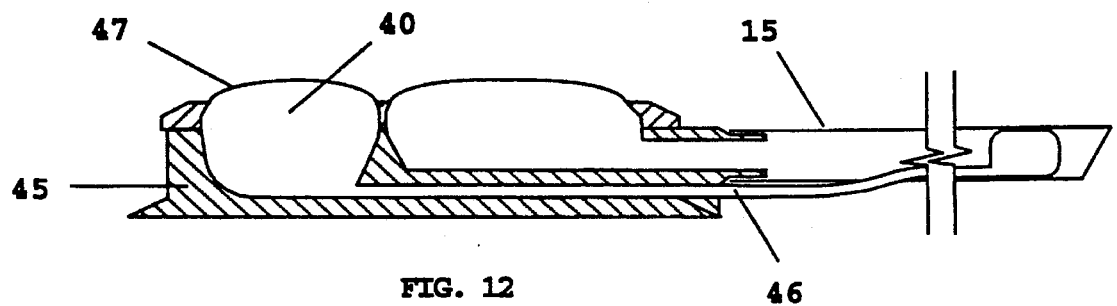
FIG. 12 shows a cross section of the embodiment of FIG. 10 along line B—B.
Figure 13:
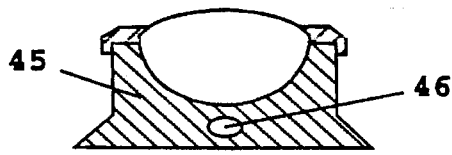
FIG. 13 shows a cross section of the embodiment of FIG. 10 along line A—A.
Figure 14:
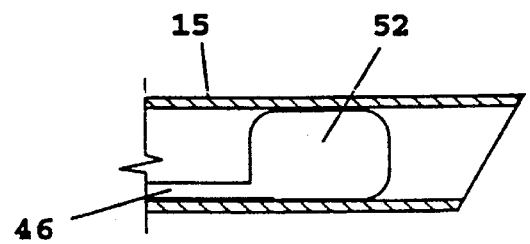
FIG. 14 shows detail of an end of the embodiment of FIG. 10.

An outlet 28 extends from the hematologic chamber 25 and serves to connect the chamber 25 with a cannula 15. The cannula 15 connects the hematologic chamber 25 to the chosen vascular structure, which may be an artery or a vein. As is best seen in FIG. 5, a slit valve 17 is provided near the end of the cannula 15. The slit valve 17 typically consists of a flat membrane of compliant material which occupies the lumen of the cannula 15. A diametrical incision or slit is located in the membrane of the slit valve 17. A cuff 16 is provided distal to the slit valve 17 at the end of the cannula 15 to facilitate the suturing of the cannula 15 to the chosen vascular structure. The cuff 16 is usually approximately 2 mm in width, but may be of any width sufficient to allow for connection of the cannula 15 to the chosen vascular structure.

The body 26 of the device 10 may be manufactured of surgical metal. Other materials of manufacture are acceptable provided they are compatible with the person or animal into which the device 10 is implanted, and do not adversely affect the tissues to which the device 10 is attached. Additionally, the body 26 should be manufactured of a material of sufficient hardness to resist being damaged or gouged by needles or other devices which will be inserted through the diaphragm 27 into the hematologic chamber 25. The diaphragm 27 should be manufactured of a material tolerant of multiple penetrations with needles or needle-introduced catheters without sacrificing the integrity of the diaphragm 27. The cannula 15 may be manufactured of PTFE, or other suitable material which is compatible with the surrounding tissues and is resistant to collapse. The cuff 16 is preferably manufactured of the same material as the cannula 15, but most importantly must be compatible with the chosen vascular structure to which it is connected. The slit valve 17 is preferably manufactured of the same material as the cannula 15, but may be manufactured of any suitable material which has sufficient flexibility to allow passage of fluid through the lumen of the cannula 15 when a pressure differential exists between the chosen vascular structure and the hematologic chamber 25, but which will also retard flow or diffusion through the lumen of the cannula 15 when no significant pressure differential exists.

The implantable vascular device 10 is used by surgically implanting the device 10 such that it is entirely subcutaneous. The distal end of the cannula 15 is connected to the chosen vascular structure. When connected to an artery or vein, the connection is usually made by grafting the cannula 15 to the artery or vein in an "end to side" manner. The connection is usually made by suturing the cuff 16 to the wall of the chosen artery or vein. The body 26 of the device 10 is attached to subcutaneous tissues to prevent undesired movement of the device 10. This is usually achieved by suturing the body 26 of the device 10 to the underlying tissue using the apertures 21. When implanted the hematologic chamber 25 of the device is filled with an anti-coagulant fluid. The slit valve 17 prevents dilution of the anti-coagulant fluid at the point of anastomosis by the blood present in the chosen artery or vein. Depending upon the frequency of use, the device may be used without a slit valve 17 or other device to prevent dilution of the anti-coagulant present in the hematologic chamber 25. During nonuse of the device there is no flow through the chamber 25, and dilution of the anti-coagulant at the point of anastomosis may occur at a slow enough rate to avoid the need for a slit valve 17 or similar apparatus if use of the device 10 is of sufficient frequency. However, use of the slit valve 17 or similar apparatus reduces the risk of thrombosis near the point of anastomosis.

After surgical implantation, the device is used by percutaneously accessing the hematologic chamber 25 through the diaphragm 27 with a needle or needle-introduced catheter. Blood may then be withdrawn from the chosen artery or vein by reducing the pressure in the hematologic chamber 25 until blood in the chosen artery or vein forces its way past the slit valve 17 into the hematologic chamber 25, and then into the needle or needle-introduced catheter penetrating the diaphragm 27. Blood or other fluid may be supplied to the person or animal into which the device 10 has been implanted by increasing the pressure in the hematologic chamber 25 until the blood or other fluid forces its way past the slit valve into the chosen artery or vein. After the blood or other fluid transfer is completed the hematologic chamber 25 is filled with anti-coagulant fluid. This serves to discourage occlusion of the cannula 15 which could be brought about by thrombosis at the point of anastomosis.

Figure 15:
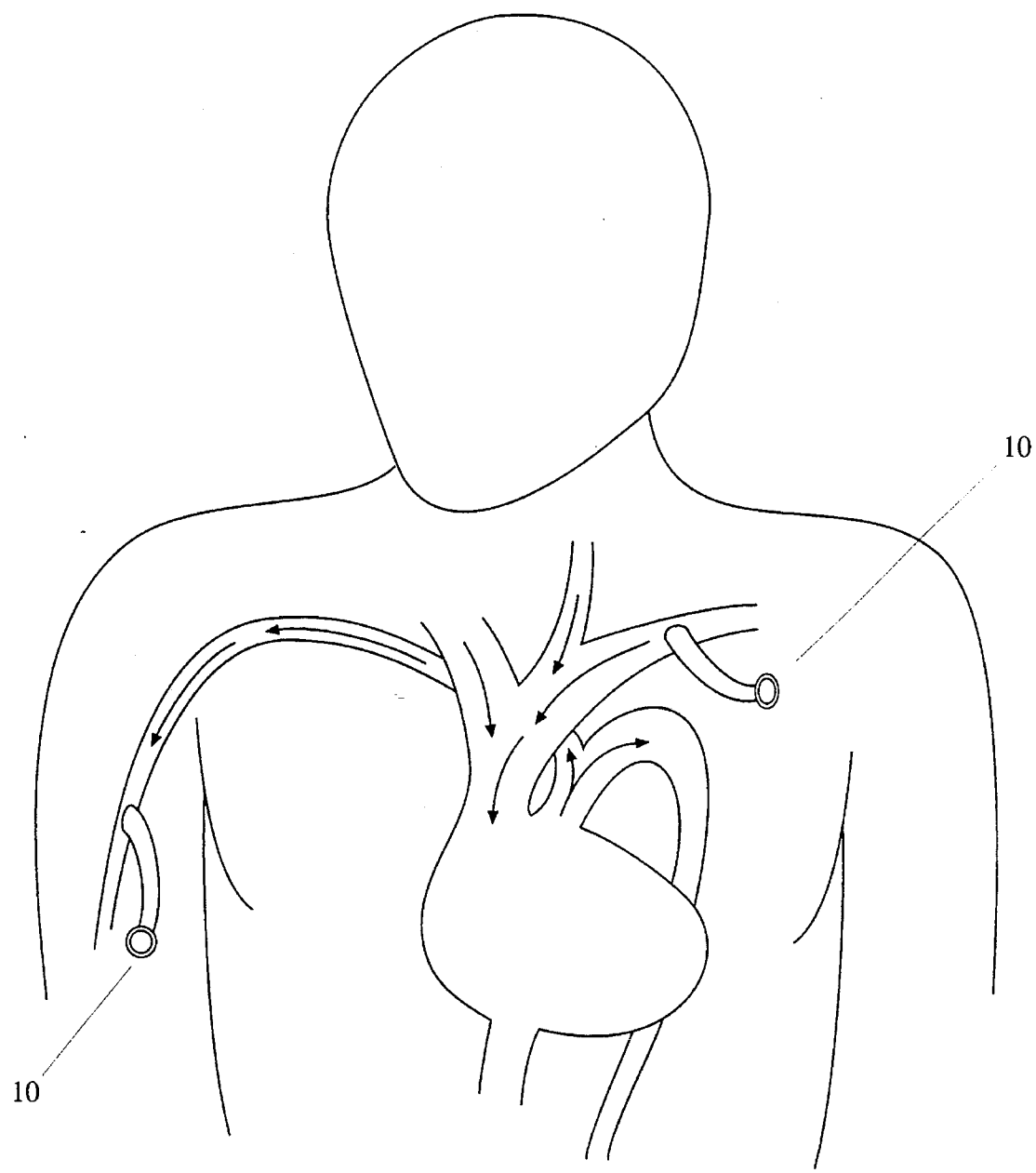

The present invention is particularly well suited for use in hemodialysis. For such use two devices 10 are surgically implanted, as shown in FIG. 15. One of the devices is grafted to an artery. The other device is grafted to a vein. In this manner both the venous and arterial circulations are accessed separately, without fistulous communication. Current use of shunts, which create a fistulous connection between artery and vein, not only involve a more extensive surgical procedure, but are fraught with problems including increased cardiac output requirements, damage to the vein due to arterial pressure waves, and frequent shunt occlusion or thrombosis. During hemodialysis, blood is removed from the hematologic chamber 25 of the device 10 grafted to an artery and is subjected to the extra-corporeal dialysis circuit. The treated blood is returned to the hematologic chamber 25 of the device 10 grafted to a vein. At the completion of the dialysis treatment both hematologic chambers 25 are filled with anti-coagulant fluid and the needles or needle-introduced catheters are removed. A similar process may be used for apheresis or exchange transfusion procedures. Additionally, the device 10 may be used for frequent administration of medication into artery or vein, or for large volume fluid infusions.

Referring to FIGS. 6 through 9, there is depicted an alternative construction of the first embodiment of the present invention. This construction of the invention employs a flap valve device 60 comprised of two sheets of compliant material 62 layered upon each other and bonded to each other along their lateral edges. This configuration allows for creation of an opening 63 between the two sheets of compliant material 62, within the cannula 15, which is created when positive pressure is achieved within the hematologic chamber or when the flap valve 60 is traversed by a percutaneous needle or needle-introduced catheter. Obliteration of the opening 63 and thus closure of the flap valve 60 is achieved by reversal of the pressure gradient attended by removal of the percutaneous needle or needle-introduced catheter and exertion of extravascular pressure upon the extralumenal portions 64 of the flap valve 60. Use of the flap valve 60 may be in conjunction with the slit valve 17, shown in FIG. 5. The hematologic chamber 25 and connecting cannula 15 are filled with anticoagulant material when not in use, with the flap valve 60 and/or the slit valve 17 preventing washout of the anticoagulant material.

Referring to FIGS. 10 through 14, them is depicted another embodiment of the present invention. In this device 30 a balloon valve 52 is substituted for the slit valve 17 of the previously described embodiment. The balloon valve is connected to a hydraulic chamber 40 defined by the body 45 of the device 30. The hydraulic chamber 40 is connected to the balloon valve 52 by a coaxial channel 46 which enters the cannula 15 and connects to the balloon valve 52. The balloon valve is inflated or deflated by the introduction or removal of sterile fluid from the hydraulic chamber 40 by means of a needle percutaneously inserted through the hydraulic chamber diaphragm 47 into the hydraulic chamber 40. The balloon valve 52 occludes the lumen of the cannula 15 when inflated. Other aspects of this embodiment of the invention are similar to those described for the other preferred embodiment.

It is intended that the foregoing detailed description be regarded as illustrative rather than limiting and that it is understood that the following claims including all equivalents are intended to define the scope of the invention.

We claim:

1. A method for using an implantable device for accessing a vascular structure in a living being, the implantable device including a hematologic chamber containing a needle-penetrable diaphragm which forms a wall of said hematologic chamber, said diaphragm being tolerant of multiple penetrations with needles or needle-introduced catheters without sacrificing the integrity of said diaphragm, said hematologic chamber being connected to one end of a cannula, the other end of said cannula being grafted to the vascular structure, whereby said hematologic chamber is in hydraulic communication with the vascular structure, said cannula containing valve means whereby hydraulic communication between said hematologic chamber and the vascular structure is prevented when said implantable device is not in use, said method comprising the steps of: surgically implanting the implantable device in a living being, whereby the end of said cannula of the implantable device not attached to said hematologic chamber is grafted to the vascular structure and whereby said hematologic chamber is attached to subcutaneous tissues such that said diaphragm is adjacent the skin of the living being, percutaneously introducing a needle or needle-introduced catheter through said diaphragm of said hematologic chamber into said hematologic chamber, altering the pressure in said hematologic chamber to initiate fluid flow, wherein decreasing the pressure is accomplished by withdrawing fluid from said hematologic chamber using the needle or needle-introduced catheter, whereby fluid is caused to flow from the vascular structure into said cannula, through said valve, into said hematologic chamber, and then into the needle or needle-introduced catheter, and wherein increasing the pressure is accomplished by injecting fluid into said hematologic chamber using the needle or needle-introduced catheter, whereby the injected fluid is caused to flow from said hematologic chamber, into said cannula, through said valve, and into the vascular structure, injecting sterile anti-coagulant fluid into said hematologic chamber of sufficient quantity to displace the fluid in said hematologic chamber and said cannula, removing the needle or needle-introduced catheter from said diaphragm.

2. A method for simultaneously using two implantable devices for accessing a vascular structure in a living being, the implantable devices each including a hematologic chamber containing a needle-penetrable diaphragm which forms a wall of said hematologic chamber, said diaphragm being tolerant of multiple penetrations with needles or needle-introduced catheters without sacrificing the integrity of said diaphragm, said hematologic chamber being connected to one end of a cannula, the other end of said cannula being grafted to the vascular structure, whereby said hematologic chamber is in hydraulic communication with the vascular structure, said cannula containing valve means whereby hydraulic communication between said hematologic chamber and the vascular structure is prevented when said implantable device is not in use, said method comprising the steps of:

surgically implanting one of the implantable devices in a living being, whereby the end of said cannula not attached to said hematologic chamber is grafted to the vascular structure, wherein the vascular structure is a vein, and whereby said hematologic chamber is attached to subcutaneous tissues such that said diaphragm is adjacent the skin of the living being, surgically implanting the other of the implantable devices in a living being, whereby the end of said cannula not attached to said hematologic chamber is grafted to the vascular structure, wherein the vascular structure is an artery, and whereby said hematologic chamber is attached to subcutaneous tissues such that said diaphragm is adjacent the skin of the living being, percutaneously introducing a needle or needle-introduced catheter through said diaphragm of said hematologic chamber into said hematologic chamber of the implantable device said cannula of which is grafted to the vascular structure, wherein the vascular structure is a vein, percutaneously introducing a needle or needle-introduced catheter through said diaphragm of said hematologic chamber into said hematologic chamber of the implantable device said cannula of which is grafted to the vascular structure, wherein the vascular structure is an artery, hydraulically connecting said percutaneously introduced needles or needle-introduced catheters with each other whereby an extra-corporeal circuit is created, said circuit containing blood handling or treating equipment such as hemodialysis equipment, decreasing the pressure in said hematologic chamber of the implantable device said cannula of which is grafted to the vascular structure, wherein the vascular structure is an artery by withdrawing fluid from said hematologic chamber using the needle or needle-introduced catheter, whereby fluid is caused to flow from the artery into said cannula, through said valve, into said hematologic chamber, and then into the needle or needle-introduced catheter, and into the extra-corporeal circuit containing blood handling or treating equipment such as hemodialysis equipment, increasing the pressure in said hematologic chamber of the implantable device said cannula of which is grafted to the vascular structure, wherein the vascular structure is a vein by injecting fluid from the extra-corporeal circuit containing blood handling or treating equipment such as hemodialysis equipment, into said hematologic chamber using the needle or needle-introduced catheter, whereby fluid is caused to flow from said hematologic chamber, into said cannula, through said valve, and into the vein, maintaining the flow of blood through the extra-corporeal circuit containing blood handling or treating equipment such as hemodialysis equipment for the time period required to adequately treat or handle the desired quantity of blood, hydraulically disconnecting said percutaneously introduced needles or needle-introduced catheters from each other, injecting sterile anti-coagulant fluid into both of said hematologic chambers of sufficient quantity to displace the fluid in said hematologic chambers and said cannula, and removing the needles or needle-introduced catheters from said diaphragms.

* * * * *